US011975010B2

(12) United States Patent
Vanleeuwen et al.

(10) Patent No.: US 11,975,010 B2
(45) Date of Patent: May 7, 2024

(54) COMPOSITIONS FOR FACILITATING TOPICAL ADMINISTRATION OF VITAMIN D WHILE PROTECTING AGAINST UV LIGHT

(71) Applicant: The Daily Suncare, LLC, Orem, UT (US)

(72) Inventors: Breelyn Jan Vanleeuwen, Orem, UT (US); Ryan Clark Roberts, Orem, UT (US)

(73) Assignee: THE DAILY SUNCARE, LLC, Orem, UT (US)

( * ) Notice: Subject to any disclaimer, the term of this patent is extended or adjusted under 35 U.S.C. 154(b) by 0 days.

(21) Appl. No.: 17/574,020

(22) Filed: Jan. 12, 2022

(65) Prior Publication Data

US 2022/0218723 A1 Jul. 14, 2022

Related U.S. Application Data

(60) Provisional application No. 63/136,800, filed on Jan. 13, 2021.

(51) Int. Cl.

| | |
|---|---|
| ***A61K 31/593*** | (2006.01) |
| ***A61K 8/27*** | (2006.01) |
| ***A61K 8/29*** | (2006.01) |
| ***A61K 9/00*** | (2006.01) |
| ***A61Q 17/04*** | (2006.01) |

(52) U.S. Cl.

CPC .............. *A61K 31/593* (2013.01); *A61K 8/27* (2013.01); *A61K 8/29* (2013.01); *A61K 9/0014* (2013.01); *A61Q 17/04* (2013.01)

(58) Field of Classification Search

None

See application file for complete search history.

(56) References Cited

U.S. PATENT DOCUMENTS

| | | | | |
|---|---|---|---|---|
| 2011/0268678 | A1 | 11/2011 | Armstrong | |
| 2012/0107255 | A1 | 5/2012 | Bonda et al. | |
| 2014/0348910 | A1 * | 11/2014 | Wright | A61P 25/28 424/59 |
| 2015/0050226 | A1 * | 2/2015 | Gardner | A61P 9/00 424/59 |
| 2016/0206543 | A1 * | 7/2016 | Tittl | A61K 9/06 |
| 2016/0331764 | A1 * | 11/2016 | Dikstein | A61K 8/345 |

FOREIGN PATENT DOCUMENTS

| | | | |
|---|---|---|---|
| EP | 0512814 | A1 | 11/1992 |
| WO | 2006/133828 | A1 | 12/2006 |

OTHER PUBLICATIONS

International Search Report and Written Opinion received for PCT Patent Application No. PCT/US2022/070181, dated Mar. 25, 2022, 9 pages.

* cited by examiner

*Primary Examiner* — Nannette Holloman
(74) *Attorney, Agent, or Firm* — Workman Nydegger

(57) ABSTRACT

This disclosure relates to a composition for facilitating transdermal delivery of vitamin D while preventing UV light from reaching user skin includes a concentration of chole-calciferol within a range of about 10 IU/g to about 40,000 IU/g. The composition includes one or more metal oxides such as zinc oxide and/or one or more titanium oxides which function to prevent (or at least limit) UV light from reaching user skin. The metal oxide(s) are provided at a concentration within a range of about 10% to about 50% by weight of the total composition.

14 Claims, No Drawings

COMPOSITIONS FOR FACILITATING TOPICAL ADMINISTRATION OF VITAMIN D WHILE PROTECTING AGAINST UV LIGHT

CROSS-REFERENCE TO RELATED APPLICATIONS

This application claims priority to and the benefit of U.S. Provisional Patent Application No. 63/136,800, filed Jan. 13, 2021, the entirety of which is incorporated herein by this reference.

BACKGROUND

A growing body of research has shown the importance of vitamin D in improving and/or maintaining bodily health. For instance, vitamin D deficiency can lead to a loss of bone density, which may lead to other conditions such as osteoporosis, rickets, and/or bone fractures. Vitamin D has also been used to treat skin diseases such as psoriasis and has even shown the ability to reduce the incidence of advanced (metastatic or fatal) cancer.

Vitamin D is also known as "the sunshine vitamin," as vitamin D synthesis occurs in the epidermis by the action of ultraviolet (UV) B light from the sun or another UVB source. However, overexposure to UVB rays present in sunlight (and/or other rays present in sunlight, such as UVA rays) can cause skin aging, skin burning (e.g., also known as "sunburn"), and can damage the DNA of skin cells. Damage to the DNA of skin cells can produce genetic defects, or mutations, that can lead to skin cancer (as well as premature aging).

Accordingly, many individuals use skin products designed to protect skin from harmful UV sunlight prior to planned prolonged exposure to sunlight (e.g., prior to participating in an outdoor activity where skin will be exposed, such as swimming). However, individuals do not commonly apply such skin protecting products on a day-to-day basis, thereby subjecting their exposed skin (e.g., facial or arm skin) to harmful UV light on a day-to-day basis. Conversely, individuals who do apply such skin protecting products on a day-to-day basis may overly limit the ability to endogenously synthesize vitamin D, which may lead to vitamin D deficiency.

Accordingly, there exists a need for compositions for facilitating transdermal delivery of vitamin D while preventing UV light from reaching user skin.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Embodiments of the present disclosure are directed to compositions for facilitating topical administration of vitamin D while protecting the skin from UV light.

In one aspect, a composition for facilitating topical administration of vitamin D while preventing UV light from reaching user skin includes a concentration of cholecalciferol (also known as vitamin $D_3$) within a range of about 10 IU/g to about 40,000 IU/g. In some instances, the composition includes one or more metal oxides (e.g., zinc oxide and/or one or more titanium oxides), which function to prevent (or at least limit) UV light from reaching user skin. The metal oxide(s) may be provided at a concentration within a range of about 2% to about 80%, or about 5% to about 50%, or about 10% to about 35%. For example, a combination of oxides may be included at a concentration of up to about 15%, up to about 20%, up to about 25%, up to about 30%, up to about 35%, up to about 40%, up to about 45%, up to about 50%, up to about 55%, up to about 60%, up to about 65%, up to about 70%, up to about 75%, up to about 80%.

In some implementations, the composition is configured to block about 50% to about 99% of light with wavelength within a range of about 290 nm to about 320 nm from reaching user skin. Furthermore, in some instances, the composition is configured to at least partially prevent or limit light with wavelength within a range of about 320 nm to about 400 nm from reaching user skin.

In some implementations, the composition is formulated as a cream, a spray, a powder, a semi-solid, a solid, a lotion, a serum, or a fluid configured for topical application to human or animal skin. In some instances, the composition includes one or more additional forms of other vitamins, such as vitamin A, vitamin E, and/or vitamin C. In some embodiments, the composition omits one or more (preferably all) of oxybenzone, avobenzone, octyl salicylate (also known as octisalate), octocrylene, homosalate, octinoxate, or polyethylene glycol.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

DETAILED DESCRIPTION

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, any headings used herein are for organizational purposes only, and the terminology used herein is for the purpose of describing the embodiments. Neither are meant to be used to limit the scope of the description or the claims.

Unless specified otherwise, where amounts are recited herein as percentages, the percentages are to be considered by weight of the overall composition. For example, a composition described as including 10% of some component will be understood to include 10% by weight of the overall composition of that component.

Embodiments of the present disclosure are directed to compositions for facilitating topical administration of vitamin D while preventing or limiting UV light from reaching user skin. The term "topical administration" can include, in at least some implementations, transdermal delivery of the vitamin D.

Those skilled in the art will appreciate, in view of the present disclosure, that at least some of the disclosed embodiments may advantageously protect users from harmful UV light while still facilitating vitamin D delivery. For example, compositions of the present disclosure may include cholecalciferol, which is also known as vitamin $D_3$ and is a type of vitamin D that is made by human skin when exposed to sunlight. In contrast with at least some other types of vitamin D, cholecalciferol may be safely and effectively delivered through the dermal route in the absence of direct UVB light to promote bodily health and to prevent vitamin D deficiency and bodily conditions that may result therefrom (e.g., psoriasis, loss of bone density etc.). Furthermore, in some implementations, compositions of the present disclosure include one or more metal oxides such as zinc oxide(s) and/or titanium oxide(s), which functions to block UV light and thereby protect user skin from the harmful effects of UV light (e.g., skin aging, sunburn, genetic mutation, etc.).

Compositions of the present disclosure may include different components and may thereby take on different forms to provide alternative ways to apply the compositions of the present disclosure to user skin. For instance, compositions of the present disclosure may be formulated as a cream, spray, powder, semi-solid, or solid that is configured for topical application to skin of a user. Accordingly, compositions of the present disclosure may be implemented to form products that allow users to easily and conveniently apply the compositions to their skin to receive the benefits provided thereby.

Products formed using compositions of the present disclosure may be beneficially formulated for use by users on a frequent basis, such as daily or even multiple times per day. Accordingly, in contrast with conventional UV protection products that may cause (or exacerbate) vitamin D deficiency if used on a daily basis, users may utilize compositions of the present disclosure to protect their skin from harmful UV light on a day-to-day basis while still receiving vitamin D to maintain and/or promote bodily health.

In accordance with the present disclosure, a composition for facilitating topical administration of vitamin D while preventing UV light from reaching user skin includes a concentration of cholecalciferol. In some instances, utilizing a concentration of cholecalciferol that is too low causes the composition to fail to facilitate adequate vitamin D delivery to a user's body to combat and/or prevent vitamin D deficiency. In contrast, in some instances, utilizing a composition of cholecalciferol that is too high causes the composition to become unstable, which may lead to a degradation and/or separation of components within the composition. Such degradation and/or separation may result in lower and/or inconsistent product effectiveness and/or shorter product shelf life. In one example, excess vitamin D may disrupt the balance in certain emulsions, reducing the stability of the composition and increasing the risk of separation of the emulsion components.

Accordingly, in some implementations, compositions of the present disclosure comprise a concentration of cholecalciferol that is beneficially within a range of about 10 IU/g to about 40,000 IU/g. In some embodiments, a concentration of cholecalciferol within a range of about 1,000 IU/g to about 20,000 IU/g is preferred, or, even more preferably, a concentration within a range of about 2,000 IU/g to about 8,000 IU/g, or, still more preferably, a concentration within a range of about 4,000 IU/g to about 6,000 IU/g. Such concentration ranges of cholecalciferol may advantageously allow sufficient vitamin D delivery to combat or prevent vitamin D deficiency in users while still allowing for an effectively stable composition.

Vitamin D levels within the foregoing ranges have also been found to be particularly effective in compositions formulated for daily use, which must additionally balance the need for an adequate dose of vitamin D with the need to avoid excessive dosing. That is, because vitamin D is fat-soluble, it is more difficult for the body to get rid of any excess amounts. Many people are deficient in vitamin D, and thus stand to benefit from additional administration. However, practical limits on the upper end of the dose should also be considered, especially for products intended for daily use.

Furthermore, in accordance with the present disclosure, a composition for facilitating transdermal delivery of vitamin D while preventing UV light from reaching user skin may include one or more metal oxides to facilitate prevention of UV light from reaching user skin. Zinc oxide is a particularly useful metal oxide for this purpose, and the following discussion will focus on its use, though it will be understood that other metal oxides (including one or more forms of titanium oxide) capable of providing a sun blocking function, while also being appropriate for topical use, may additionally or alternatively be included. When disposed on user skin, such metal oxides may provide a physical barrier between harmful UV light and the user skin and thereby protect the user skin from damage that may otherwise result from exposure to UV light. Zinc oxide and certain titanium oxides are furthermore believed to be safe for use on human skin and are regarded as comparatively safe for the environment (e.g., as compared to certain chemicals used in conventional sun protection products, as discussed hereinafter).

As the skilled person recognizes, the term "titanium oxide" is a general term that encompasses several different forms, including titanium dioxide (also known as titanium (IV) oxide), titanium monoxide (also known as titanium monoxide), dititanium trioxide (also known as Titanium(III) oxide), $Ti_3O$, $Ti_2O$, and other forms according to $Ti_nO_{2n-1}$ (n=3-9). As used herein, the terms titanium oxide or titanium oxides will be understood to refer to any combination of one or more of such forms. In presently preferred embodiments, most or all of the titanium oxide is of the titanium dioxide form.

In some instances, utilizing a concentration of metal oxide(s) that is too low causes the composition to fail to provide sufficient protection from UV light to ameliorate adverse effects caused by exposure to UV light (e.g., skin aging, sunburn, genetic mutation, etc.). In contrast, utilizing a concentration of metal oxide(s) that is too high may result in a composition that, when applied to user skin, adversely affects the appearance of the user's skin, such as by altering the appearance of the tone, hue, reflectivity, complexion and/or other attributes of the skin of the user.

Accordingly, in some embodiments, compositions of the present disclosure include a concentration of metal oxide(s) that is within a range of about 2% to about 80%, or more preferably about 10% to about 50%. In some embodiments, zinc oxide is included within a range of about 1% to about 40%, preferably at a concentration of at least about 10%. In some embodiments, one or more titanium oxides are included within a range of about 1% to about 40%, such as about 1% to about 10%. The concentration of metal oxide(s) in a composition of the present disclosure may depend, in some instances, on the product formulation of the composition. By way of non-limiting example, a composition of the present disclosure formulated as a topical cream, spray, or powder may include a concentration of metal oxide(s) within a range of about 10% to about 50%, or about 10% to about 25%, whereas a composition of the present disclosure formulated as a solid or semi-solid configured for topical application may include a concentration of metal oxide(s) within a range of about 5% to about 10%.

Such concentration ranges of metal oxide(s) may advantageously facilitate sufficient protection of user skin from UV rays while avoiding adverse effects on the visual appearance of user skin. Such concentration ranges of metal oxide(s) may enable compositions of the present disclosure to facilitate prevention of about 50% to about 99% of UVB light from reaching user skin when disposed thereover. As used herein, UVB light refers to light that includes one or more wavelengths within a range of about 290 nm to about 320 nm. Furthermore, such concentration ranges of metal oxide(s) may provide compositions with a sun protection factor (SPF) within a range of about 2 to about 100, or more preferably within a range of about 30 to 60.

Furthermore, in some instances, the concentration ranges of metal oxide(s) described herein may provide compositions that are configured to at least partially prevent UVA light from reaching user skin when disposed thereover. As used herein, UVA light refers to light that includes one or more wavelengths within a range of about 320 nm to about 400 nm.

Although the present disclosure focuses, in at least some respects, on utilizing zinc oxide as a component for facilitating protection of user skin from UV light, compositions of the present disclosure may additionally or alternatively include one or more titanium oxides (e.g., titanium oxide and/or titanium dioxide) and/or other metal oxides to facilitate protection of user skin from UV light. For example, the topical cream and topical powder example formulations described herein with reference to “Example 1” and “Example 3”, respectively, include titanium dioxide in addition to zinc oxide for facilitating protection of user skin from UV light.

The use of zinc oxide and/or one or more titanium oxides in compositions of the present disclosure to facilitate protection of user skin from UV rays is in contrast with many conventional sunlight protection products, known conventionally and referred to herein as “sunscreens”. For example, many sunscreen products include chemicals such as oxybenzone, avobenzone, octisalate, octocrylene, homosalate, octinoxate, and/or others. When applied to user skin, such chemicals penetrate the user skin to absorb UV rays before the UV rays can cause damage to the user skin. Although many conventional sunscreen products that implement such chemicals appear to provide adequate UV ray protection for users, the extent of bodily damage caused by chemicals such as oxybenzone, avobenzone, octisalate, octocrylene, homosalate, and/or octinoxate remains unknown, and the long-term effects of such compounds are particularly questionable. Thus, many users refrain from using such sunscreen products on a day-to-day basis and only use such sunscreen products on an infrequent basis in anticipation of a planned extended period of exposure to sunlight. Furthermore, such sunscreen products also often need to be reapplied frequently to provide adequate UV protection and require a period of time to absorb into user skin before UV protection triggers.

Thus, in at least some instances, compositions of the present disclosure advantageously omit chemicals such as oxybenzone, avobenzone, octisalate, octocrylene, homosalate, and octinoxate. Accordingly, compositions of the present disclosure avoid the cloud of uncertainty of bodily effects associated with products that include such chemicals. Thus, users should be more comfortable utilizing compositions of the present disclosure on a day-to-day basis to attain benefits associated with compositions of the present disclosure, such as receiving vitamin D and receiving protection against UV light. Furthermore, by avoiding chemicals such as oxybenzone, avobenzone, octisalate, octocrylene, homosalate, and/or octinoxate, compositions of the present disclosure may provide immediate protection against UV rays on application to user skin, in contrast with conventional sunscreen products that require absorption into user skin before providing protection against UV rays.

As indicated hereinabove, compositions of the present disclosure may implement various different types of components to formulate different types of products for use by users. Users may apply the various types of formulations on their skin to receive the benefits facilitated by the disclosed compositions. By way of non-limiting example, compositions of the present disclosure may be formulated as a cream, spray, powder, solid, and/or other form for application to human skin.

A number of specific example compositions for facilitating topical administration of vitamin D while preventing UV light from reaching user skin will now be discussed. One will appreciate, in view of the present disclosure, that the specific components and/or concentrations included hereinbelow according to the following examples are provided by way of non-limiting example only and that additional or alternative components and/or concentrations (e.g., functional equivalents to those described hereinbelow) may be used in combination with cholecalciferol, zinc oxide, and/or titanium oxide(s) (e.g., titanium oxide and/or titanium dioxide) to provide a composition for facilitating transdermal delivery of vitamin D while preventing UV light from reaching user skin.

EXAMPLES

Example 1

In one example, a composition for facilitating transdermal delivery of vitamin D while preventing UV light from reaching user skin is formulated as a cream or lotion configured for topical application to skin. For instance, such a cream or lotion may include a concentration of water within a range of about 50% to about 75%, zinc oxide within a range of about 10% to about 40%, caprylic/capric triglyceride within a range of about 5% to about 10%, titanium dioxide within a range of about 1% to about 10%, glycerin within a range of about 1% to about 5%, polyglyceryl-4 diisostearate/polyhydroxystearate/sebacate within a range of about 1% to about 5%, *Simmondsia chinensis* (jojoba) seed oil within a range of about 1% to about 5%, sodium chloride within a range of about 1% to about 5%, stearic acid within a range of about 0.1% to about 1%, phenoxyethanol within a range of about 0.1% to about 1%, aloe barbadensis leaf extract within a range of about 0.1% to about 1%, tetrahexyldecyl ascorbate within a range of about 0.1% to about 1%, xanthan gum within a range of about 0.1% to about 1%, and cholecalciferol within a range of about 10 IU/g to about 40,000 IU/g. Furthermore, in some instances, a cream or lotion may further include a concentration of up to about 0.1% disodium EDTA, up to about 0.1% tocopherol, and up to about 0.1% tocopheryl acetate.

The following table illustrates ingredient and concentration ranges in accordance with International Nomenclature of Cosmetic Ingredients (INCI) convention for a composition of the present disclosure formulated as a cream or lotion configured for topical application to skin.

| INCI (US) | % Range |
|---|---|
| Water | [50%-75%] |
| Zinc Oxide | [10%-50%] |
| Caprylic/Capric Triglyceride | [5%-10%] |
| Titanium Dioxide | [1%-10%] |
| Glycerin | [1%-5%] |
| Polyglyceryl-4 Diisostearate/ Polyhydroxystearate/Sebacate | [1%-5%] |
| Simmondsia Chinensis (Jojoba) Seed Oil | [1%-5%] |
| Sodium Chloride | [1%-5%] |
| Stearic Acid | [0.1%-1%] |
| Phenoxyethanol | [0.1%-1%] |
| Aloe Barbadensis Leaf Extract | [0.1%-1%] |
| Tetrahexyldecyl Ascorbate | [0.1%-1%] |
| Xanthan Gum | [0.1%-1%] |
| Disodium Edta | [0%-0.1%] |
| Tocopherol | [0%-0.1%] |
| Tocopheryl Acetate | [0%-0.1%] |
| Cholecalciferol | [10 IU/g- 40,000 IU/g] |

As is evident from the foregoing table, a composition for facilitating topical administration of vitamin D while preventing UV light from reaching user skin may include ingredients associated with vitamins other than vitamin D. For example, the formulation indicated by the foregoing table includes tocopherol and tocopheryl acetate, which are forms of vitamin E that may be delivered through the dermal route. Furthermore, the formulation indicated by the foregoing table include tetrahexyldecyl ascorbate, which is a form of vitamin C that is lipid-soluble that may be delivered through the dermal route. It is theorized that the addition of such lipid-soluble vitamins, when provided in amounts within the ranges described herein, can aid in the delivery of vitamin D to the user such that a higher proportion of the vitamin D is taken up and made available to the user. These components are also applicable to the other examples described herein.

Accordingly, a composition of the present disclosure may include one or more forms of one or more other vitamins, such as vitamin E or vitamin C, to produce synergistic effects among the vitamins included, such as improving immune function, ameliorating symptoms of various types of infections, and/or others. Furthermore, one will appreciate, in view of the present disclosure, that a composition of the present disclosure may include forms of other types of vitamins not explicitly shown in the example provided herein, such as forms of vitamin A (e.g., retinol, retinal, retinoic acid, retinyl ester, etc.). These components are also applicable to the other examples described herein.

Furthermore, as is evident from the foregoing table, a composition for facilitating transdermal delivery of vitamin D while preventing UV light from reaching user skin may include various types of skin conditioners, such as *Simmondsia chinensis* (jojoba) seed oil, aloe barbadensis leaf extract, and/or others shown in the foregoing and other tables included in the present disclosure. Implementing skin conditioners into compositions of the present disclosure may allow the compositions to improve the health of user skin and thereby improve the ability of user skin to utilize vitamin D and/or other vitamins present in the compositions. Skin conditioners may also provide other desirable effects on user skin, such as a moisturizing effect, a soothing effect, and/or others, which can improve user comfort when using compositions of the present disclosure in an everyday manner. In this regard, implementing skin conditioners into compositions of the present disclosure may advantageously improve user comfort when using compositions of the present disclosure and may motivate users to use compositions of the present disclosure on a more frequent basis (e.g., daily). These components are also applicable to the other examples described herein.

Example 2

In another example, a composition for facilitating transdermal delivery of vitamin D while preventing UV light from reaching user skin is formulated as spray configured for topical application to skin. For instance, such a spray may include a concentration of water within a range of about 50% to about 75%, zinc oxide within a range of about 10% to about 50%, coco-caprylate within a range of about 10% to about 25%, pentylene glycol within a range of about 1% to about 5%, polyhydroxystearic acid within a range of about 1% to about 5%, sorbitan isostearate within a range of about 0.1% to about 1%, sorbitan laurate within a range of about 0.1% to about 1%, hydroxyacetophenone within a range of about 0.1% to about 1%, behenyl alcohol within a range of about 0.1% to about 1%, glyceryl behenate within a range of about 0.1% to about 1%, cetearyl alcohol within a range of about 0.1% to about 1%, benzyl alcohol within a range of about 0.1% to about 1%, xanthan gum within a range of about 0.1% to about 1%, and cholecalciferol within a range of about 10 IU/g to about 40,000 IU/g. Furthermore, in some instances, a spray may further include a concentration of up to about 0.1% sodium phytate, up to about 0.1% panthenol, and up to about 0.1% alcohol.

The following table illustrates ingredient and concentration ranges in accordance with INCI convention for a composition of the present disclosure formulated as a spray configured for topical application to skin.

| INCI (US) | % Range |
|---|---|
| Water | [50%-75%] |
| Zinc Oxide | [10%-50%] |
| Coco-Caprylate | [10%-25%] |
| Pentylene Glycol | [1%-5%] |
| Polyhydroxystearic Acid | [1%-5%] |
| Sorbitan Isostearate | [0.1%-1%] |
| Sorbitan Laurate | [0.1%-1%] |
| Hydroxyacetophenone | [0.1%-1%] |
| Behenyl Alcohol | [0.1%-1%] |
| Glyceryl Behenate | [0.1%-1%] |
| Cetearyl Alcohol | [0.1%-1%] |
| Benzyl Alcohol | [0.1%-1%] |
| Xanthan Gum | [0.1%-1%] |
| Sodium Phytate | [0%-0.1%] |
| Panthenol | [0%-0.1%] |
| Alcohol | [0%-0.1%] |
| Cholecalciferol | [10 IU/g- 40,000 IU/g] |

Example 3

In another example, a composition for facilitating transdermal delivery of vitamin D while preventing UV light from reaching user skin is formulated as a powder configured for topical application to skin (e.g., via an applicator brush or other type of applicator). For instance, such a powder may include a concentration of mica within a range of about 50% to about 75%, zinc oxide within a range of about 10% to about 40%, titanium dioxide within a range of about 1% to about 25% (e.g., 1%, 5%, 10%, 15%, 20%, 25%, or a range with endpoints defined by any two of the foregoing values), silica within a range of about 1% to about 5%, triethoxycaprylylsilane within a range of about 1% to about 5%, and cholecalciferol within a range of about 10 IU/g to about 40,000 IU/g. Furthermore, in some instances, a powder may further include a concentration of up to about 0.1% iron oxides.

The following table illustrates ingredient and concentration ranges in accordance with INCI convention for a composition of the present disclosure formulated as a powder configured for topical application to skin.

| INCI (US) | % Range |
|---|---|
| Mica | [50%-75%] |
| Zinc Oxide | [10%-40%] |
| Titanium Dioxide | [1%-25%] |
| Silica | [1%-5%] |
| Triethoxycaprylylsilane | [1%-5%] |
| Iron Oxides | [0%-0.1%] |
| Cholecalciferol | [10 IU/g-] 40,000 IU/g |

Example 4

In another example, a composition for facilitating transdermal delivery of vitamin D while preventing UV light from reaching user skin is formulated as a solid or semi-solid configured for topical application to skin (e.g., a solid in the form of a "stick" that can be pressed over user skin to dispose the composition thereon, similar to stick deodorant). For instance, such a solid or semi-solid may include a concentration of *Ricinus communis* (castor) seed oil within a range of about 25% to about 50%, *Helianthus annuus* (sunflower) seed wax within a range of about 10% to about 25%, *Prunus amygdalus dulcis* (sweet almond) oil within a range of about 10% to about 25%, *Simmondsia chinensis* (jojoba) seed oil within a range of about 5% to about 10%, zinc oxide within a range of about 5% to about 50% (e.g., 5%, 10%, 15%, 20%, 25%, 30%, 35%, 40%, 45%, 50%, or a range with endpoints defined by any two of the foregoing values), beeswax within a range of about 1% to about 5%, jojoba esters within a range of about 1% to about 5%, polyhydroxystearic acid within a range of about 0.1% to about 1%, tocopherol within a range of about 0.1% to about 1%, and cholecalciferol within a range of about 10 IU/g to about 40,000 IU/g.

The following table illustrates ingredient and concentration ranges in accordance with INCI convention for a composition of the present disclosure formulated as a solid configured for topical application to skin.

| INCI (US) | % Range |
|---|---|
| Ricinus Communis (Castor) Seed Oil | [25%-50%] |
| Helianthus Annuus (Sunflower) Seed Wax | [10%-25%] |
| Prunus Amygdalus Dulcis (Sweet Almond) Oil | [10%-25%] |
| Simmondsia Chinensis (Jojoba) Seed Oil | [5%-10%] |
| Zinc Oxide | [5%-50%] |
| Beeswax | [1%-5%] |
| Jojoba Esters | [1%-5%] |
| Polyhydroxystearic Acid | [0.1%-1%] |
| Tocopherol | [0.1%-1%] |
| Cholecalciferol | [10 IU/g-40,000 IU/g] |

As is evident from the foregoing examples, compositions of the present disclosure may omit polyethylene glycol (PEG), which is an emulsifying agent commonly found in many skin care products, particularly creams and lotions. The extent of bodily damage that can be caused by long-term use of PEG remains unknown. Accordingly, in at least some implementations, compositions of the present disclosure for facilitating transdermal delivery of vitamin D while preventing UV light from reaching user skin advantageously omit PEG and thereby avoid the uncertainty of bodily effects associated with products that include PEG. Accordingly, users should be more comfortable utilizing compositions of the present disclosure on a day-to-day basis to attain benefits associated with compositions of the present disclosure.

Although the above examples are directed to particular forms of the disclosed compositions, other embodiments may provide the composition in a different form, such as a lotion, serum, or fluid suitable for topical administration.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may also include properties and/or features (e.g., ingredients, components, members, elements, parts, and/or portions) described in one or more separate embodiments and are not necessarily limited strictly to the features expressly described for that particular embodiment. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

What is claimed is:

1. A composition for facilitating topical administration of vitamin D while preventing or limiting ultraviolet (UV) light from reaching user skin, the composition consisting of:

cholecalciferol included at a concentration of about 10 IU/g to about 40,000 IU/g;

one or more metal oxides to facilitate prevention of UV light from reaching user skin;

one or more carrier components to formulate the composition as a cream, spray, powder, solid, semi-solid, lotion, serum, or fluid for topical application;

optionally, one or more additional vitamins selected from vitamin A, vitamin E, vitamin C, or a combination thereof; and optionally, one or more skin conditioners.

2. The composition of claim 1, wherein the cholecalciferol is included within a range of about 1,000 IU/g to about 20,000 IU/g.

3. The composition of claim 1, wherein the vitamin C comprises a lipid-soluble form of vitamin C.

4. The composition of claim 1, wherein the one or more metal oxides comprise zinc oxide.

5. The composition of claim 4, wherein the zinc oxide is included at a concentration of about 1% to about 40% by weight of the composition.

6. The composition of claim 1, wherein the one or more metal oxides comprise one or more titanium oxides.

7. The composition of claim 6, wherein the one or more titanium oxides are included at a concentration of about 1% to about 40% by weight of the composition.

8. The composition of claim 1, wherein the one or more metal oxides comprise up to about 0.1% iron oxides by weight of the composition.

9. The composition of claim 1, wherein a concentration of the one or more metal oxides is within a range of about 10% to about 50% by weight of the composition.

10. The composition of claim 1, wherein the cholecalciferol is included within a range of about 4,000 IU/g to about 6,000 IU/g.

11. The composition of claim 1, wherein the composition is formulated as a cream configured for topical application.

12. The composition of claim 1, wherein the composition is formulated as a spray configured for topical application.

13. The composition of claim 1, wherein the composition is formulated as a powder configured for topical application.

14. The composition of claim 1, wherein the composition is formulated as a solid or semi-solid configured for topical application.

* * * * *